US006358228B1

United States Patent
Tubman et al.

(10) Patent No.: US 6,358,228 B1
(45) Date of Patent: Mar. 19, 2002

(54) VASOOCCLUSIVE DEVICE INCLUDING ASYMMETRICAL PLURALITIES OF FIBERS

(75) Inventors: David E. Tubman, Edina, MN (US); Thomas A. Osborne, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 0 days.

(21) Appl. No.: 09/286,774

(22) Filed: Apr. 6, 1999

Related U.S. Application Data

(60) Provisional application No. 60/081,000, filed on Apr. 7, 1998.

(51) Int. Cl.[7] ............................................. A61M 29/00
(52) U.S. Cl. .................... 604/104; 604/96.01; 606/194; 606/200; 606/151
(58) Field of Search .......................... 604/96, 104, 194, 604/96.01; 606/194, 191, 151, 198, 200

(56) References Cited

U.S. PATENT DOCUMENTS

| 5,304,194 A | 4/1994 | Chee et al. |
| 5,423,849 A | 6/1995 | Engelson et al. |
| 5,476,472 A | * 12/1995 | Dormandy, Jr. et al. ...... 604/96 |
| 5,522,822 A | 6/1996 | Phelps et al. |
| 5,549,624 A | 8/1996 | Mirigian et al. |
| 5,658,308 A | 8/1997 | Snyder |
| 5,843,118 A | 12/1998 | Sepetka et al. |

FOREIGN PATENT DOCUMENTS

| EP | 0778006 | * 6/1997 |
| EP | WO-0778006 | * 6/1997 |
| WO | 9409705 | 5/1994 |
| WO | 9409706 | 5/1994 |
| WO | 9509567 | 4/1995 |

OTHER PUBLICATIONS

Gianturco, C. et al., "Mechanical Devices For Arterial Occlusion", *The American Journal of Roentgenology, Radium Therapy and Nuclear Medicine,* vol. 124, No. 3, Jul. 1975, pp. 428–435.

* cited by examiner

*Primary Examiner*—Anhtuan T. Nguyen
*Assistant Examiner*—Michael M Thompson
(74) *Attorney, Agent, or Firm*—Richard J. Godlewski

(57) ABSTRACT

A vasoocclusive device 10 is adapted for introduction into a vessel of a human or veterinary patient and occluding flow through the vessel. The device 10 includes a radiopaque member 12 (such as a metallic coil 14) having a proximal end 16 and a distal end 18, the distal end 18 being introduced first into the vessel. The member 12 is about 1.5 mm to about 3.0 mm long and no more than about 2.7 mm wide, preferably about 0.25 to 0.4 mm wide. The device 10 also includes a distal plurality 20 of fibers having an average distal fiber length, associated with and extending away from the distal end 18 of the member 12, as well as a proximal plurality 24 of fibers having an average proximal fiber length, associated with and extending away from the proximal end 16 of the member 12. The average proximal fiber length is about two to about five times the average distal fiber length. The average distal fiber length is preferably about 4 to 8 mm, while the average proximal fiber length is preferably about 9 to 15 mm. The distal and proximal pluralities 20 and 24 of fibers each preferably include 8 to 10 individual fibers composed of polyester, nylon or silk of about 40 denier. The vasoocclusive device 10 is particularly advantageous in that it can be used in vessels which are significantly narrower than those in which prior devices could be used, yet its asymmetric arrangement of the distal and proximal pluralities 20 and 24 of fibers allows it to enjoy significantly improved lodging in such narrow vessels.

36 Claims, 3 Drawing Sheets

VASOOCCLUSIVE DEVICE INCLUDING ASYMMETRICAL PLURALITIES OF FIBERS

CROSS-REFERENCE TO RELATED APPLICATIONS

This application claims priority of provisional application Ser. No. 60/081,000, filed Apr. 7, 1998.

TECHNICAL FIELD

This invention relates generally to medical devices, and more particularly to devices for occluding a vessel of a human or veterinary patient.

BACKGROUND OF THE INVENTION

Vasoocclusive devices are surgical implants which are placed within the blood vessels or vascular cavities (hereinafter, "vessels") of a human or veterinary patient. Vasoocclusive devices form an occlusion, thrombus, embolism, blockage or the like in the vessel at the site of implantation. Sites of interest are often the cranial arteries but may be any other site where occlusion is desired.

There are a number of reasons why it may be desirable to occlude a vessel. For example, the site of a stroke or other vascular accident can be treated by placing an occlusive device proximal of the site to block the flow of blood to the site, thereby alleviating leakage at the site. An aneurysm can be treated by the introduction of a vasoocclusive device through the neck of the aneurysm; the thrombogenic nature of the device causes a mass to form in the aneurysm and lowers the potential for growth of the aneurysm and its subsequent rupture. Other diseases, such as tumors and the like, can be treated by occluding the flow of blood to a targeted site of interest.

Several known vasoocclusive devices include a coil having a plurality of fibers, threads, strands or the like (hereinafter, "fibers") extending either laterally of the coil, or connected to and extending along the side of the coil, or extending from an end of the coil. The fibers can be loops or can have free ends. Such devices are typically implanted by the use of a catheter introduced into the bloodstream at a convenient site, often the femoral artery in the groin, and advanced to the site of interest. More particularly, such devices are often supplied in prepackaged form in a sterile cannula which is adapted to engage the proximal end of a catheter. Once the catheter is in place within a vessel of interest, the coil-containing cannula is placed in engagement with the proximal end of the catheter, and the coil is transferred from the cannula and into the catheter by exerting a force on the proximal end of the coil. A pusher rod is then used to push the coil through the catheter to the site at which release of the coil is desired. Typically, the coil is radiopaque, permitting its location to be visualized. Once the coil is at the site of interest, the pusher rod is used to plunge the coil from the catheter and into the vessel. The fibers or fiber loops on the coil extend outwardly from the coil surface to fill the vessel.

While such vasoocclusive devices are generally useful for their intended purpose, their use can be subject to several practical drawbacks. Perhaps most importantly, conventional vasoocclusive devices are often not useful in relatively small vessels such as cranial vessels. More specifically, such prior devices are often useful only in vessels exceeding about 2.7 mm in diameter.

A variety of other objects have been used in an attempt to occlude these smaller vessels. Such other objects have included bits of blood clot, silicone spheres, long or short pieces of wire guide material, polyester (for example, DACRON®) fibers, silk threads and bits of Gelfoam. All of these have the advantage over coil-type devices in that they can be injected into the vessel of interest through a micro catheter such as the COOK® MICROFERRET™ (a trademark of Cook Incorporated, Bloomington, Ind.). Saline or a contrast agent is typically used to inject the object through the micro catheter.

While the injection of such objects is advantageous in that the need for a pusher rod (wire guide) is eliminated, their use is subject to practical drawbacks. Most notably, any such object that is small enough to be delivered through a small bore catheter is not large enough to lodge well in the target vessel and form an effective occlusion. While such objects can be injected easily, once they leave the tip of the catheter they continue to travel along the vessel until they reach some sort of restriction in which they can become lodged. The occlusion is then formed wherever such lodging occurs. The physician has to be very careful when injecting such objects to ensure that the occlusion will occur in a useful place. Quite simply, the physician cannot simply expect the occlusion to occur at or near the catheter tip; to the contrary, the physician has little control over where the occluding object will lodge. Unfortunately, the occluding device may travel too far downstream in the vessel, and may even lodge in a place where the device may do more harm than good for the patient.

It would be highly desirable to have a vasoocclusive device whose lodging in a vessel was very reliable and whose positioning could be controlled with great precision. It would also be highly desirable to have such a device which could be used in vessels of very small diameter, in particular, in vessels having a diameter below about 2.7 mm. It would further be highly desirable to have such a device which could be introduced into a patient by injection with a fluid, rather than by being pushed with a rod or the like.

SUMMARY OF THE INVENTION

The foregoing problems are solved and a technical advance is achieved in an illustrative vasoocclusive device which is particularly useful in small vessels, preferably in cranial vessels smaller than about 2.7 mm in diameter. Like coil-type devices useful in larger vessels, the device of the present invention comprises a central member and a plurality of fibers or the like extending from the ends of the central member. Advantageously, the member can be significantly smaller than the coils employed in prior coil-type devices. However, the pluralities of fibers on the ends of the member are asymmetric; that is, the fibers on one end of the member are, on average, significantly longer than the fibers on the other end of the member. In particular, the average fiber length on the end of the member which leads the device during its introduction (designated herein as the "distal" end of the member) is only about 20 percent to about 50 percent of the average fiber length on the trailing end of the member (designated herein as the "proximal" end of the member). Stated alternatively, the average proximal fiber length is about 2 to about 5 times as great as the average distal fiber length.

This asymmetric arrangement of the fibers on the ends of the central member of the device of the present invention is particularly advantageous in that the device lodges quite well immediately upon expulsion from the catheter, rather than migrating in the vessel before lodging. This reliable lodging gives the physician significantly more confidence about and precise control over the position of the occlusion formed by the device. Of course, unlike the prior coil-type devices, the vasoocclusive device of the present invention can be injected through a micro catheter, obviating the need for a pusher rod or wire guide.

The superior performance of the vasoocclusive device of the present invention appears to result from the asymmetric arrangement of the fibers on the end of the central member. More particularly, it appears that as the device is expelled from the tip of the micro catheter, it is traveling some small amount faster than the blood in the vessel. As a result, the shorter, leading distal fibers tend to spread out and create some drag against the vessel wall. This drag slows the device to a little less than the velocity of the blood. As a result of such slowing, the longer, trailing proximal fibers begin to spread out and bunch up around the central member. The flow of blood increases the pressure on the proximal fibers, and this pressure is transferred by the central member to the distal fibers, causing the distal fibers to bunch up tighter ahead of the member. Such bunching increases the effective cross-sectional area of the device and causes the device to lodge immediately and reliably, and block blood flow through the vessel. Preferably, both the proximal and distal fibers are longer than the central member, facilitating reliable lodging. The improved lodging which results from this "drag differential" between the shorter distal fibers and the longer proximal fibers is quite pronounced, in contrast to fibers alone, and in contrast to devices having fibers on only one end of a central coil or having fibers of equal length.

In a first aspect, then, the present invention is directed to a vasoocclusive device adapted for introduction into a vessel of a human or veterinary patient and capable of occluding a flow in the vessel when introduced into the vessel, comprising: a member having a proximal end and a distal end spaced from the proximal end, the distal end of the member being introduced into the vessel before the proximal end of the member is introduced into the vessel; a distal plurality of fibers having an average distal fiber length, the distal plurality of fibers being associated with and extending away from the distal end of the member; and a proximal plurality of fibers having an average proximal fiber length, the proximal plurality of fibers being associated with and extending away from the proximal end of the member; wherein the average proximal fiber length is greater than the average distal fiber length.

Preferably, the average proximal fiber length is about two to about five times the average distal fiber length, while both the average distal fiber length and the average proximal fiber length are greater than the length of the member, that is, greater than the distance between the proximal end and the distal end of the member. More preferably, the average distal fiber length is about 4 mm to about 8 mm, and the average proximal fiber length is about 9 mm to about 15 mm. The distal and proximal pluralities of fibers each preferably comprise 8 to 10 individual fibers composed of 40 denier polyester (for example, DACRON®), nylon or silk.

Also preferably, the member is radiopaque and is cylindrical in shape. The member can be a segment of cannula or plastic tubing. In such a case, the proximal plurality of fibers can be formed continuously with the distal plurality of fibers, and can be secured inside the segment with a medical grade adhesive. Alternatively, the proximal and distal pluralities of fibers can be formed from a plurality of individual fibers joined at a location significantly offset from their centers. The individual fibers can be joined by gluing, knotting or the like; the locus at which they are joined will have an appreciable length (that is, the locus will be at least a few times longer than the diameter of the individual fibers), so that the member comprises the locus of such joining. It is still sensible to refer to the locus of such joining as having proximal and distal ends.

It is preferred, however, that the member is a coil of platinum, stainless steel or tungsten, the coil having a plurality of windings. The distal and proximal pluralities of fibers can then be trapped between the windings of the coil if adjacent windings of the coil abut one another, or can be wrapped about single windings of the coil if adjacent windings of the coil do not abut one another. The length of the member, that is, the distance between its proximal and distal ends, can be about 1.5 mm to about 3.0 mm. The member is preferably no more than about 2.7 mm wide, and more preferably about 0.25 mm to about 0.4 mm wide.

In a second aspect, the present invention is directed to a device of the type disclosed above, comprising a specific combination of the preferred elements disclosed above. More particularly, in this second aspect, the present invention is directed to a vasoocclusive device adapted for introduction into a vessel of a human or veterinary patient and capable of occluding a flow in the vessel when introduced into the vessel, comprising: a radiopaque member having a proximal end and a distal end spaced from the proximal end, the distal end of the member being introduced into the vessel before the proximal end of the member is introduced into the vessel, and the member being about 1.5 mm to about 3.0 mm in length; a distal plurality of fibers having an average distal fiber length, the distal plurality of fibers being associated with and extending away from the distal end of the member; and a proximal plurality of fibers having an average proximal fiber length, the proximal plurality of fibers being associated with and extending away from the proximal end of the member; wherein the average proximal fiber length is about two to about five times the average distal fiber length, the average distal fiber length is about 4 mm to about 8 mm and the average proximal fiber length is about 9 mm to about 15 mm; wherein the average distal fiber length and the average proximal fiber length are both greater than the length of the member; wherein the member comprises a cylindrical coil of platinum, stainless steel or tungsten including a plurality of abutting windings; wherein the distal plurality of fibers comprises 8 to 10 individual distal fibers comprising polyester, nylon or silk of about 40 denier, and the proximal plurality of fibers comprises 8 to 10 individual proximal fibers comprising polyester, nylon or silk of about 40 denier; and wherein the member is about 0.25 mm to about 0.4 mm wide.

In a final aspect, the present invention is directed to an improvement in a vasoocclusive device adapted for introduction into a vessel of a human or veterinary patient and capable of occluding a flow in the vessel when introduced into the vessel, the device comprising: a member having a proximal end and a distal end spaced from the proximal end, the distal end of the member being introduced into the vessel before the proximal end of the member is introduced into the vessel; a distal plurality of fibers having an average distal fiber length, the distal plurality of fibers being associated with and extending away from the distal end of the member; and a proximal plurality of fibers having an average proximal fiber length, the proximal plurality of fibers being associated with and extending away from the proximal end of the member; the improvement wherein the average proximal fiber length is greater than the average distal fiber length.

In this final aspect of the invention, the designation of one end of the member in this general type of device as "proximal" and the other end of the member as "distal" is arbitrary, and merely indicates that prior devices of this general type were in fact inserted into vessels one end before the other. This arbitrary designation does not mean that the proximal and distal ends of any prior device of this general type were distinguishable from one another in any way, nor does it mean that those skilled in the art have recognized any difference between the end of the device inserted first and the end of the device inserted second. Instead, the proximal and distal ends of the prior devices of this general type appear to be completely symmetric in their possession and arrangement of fibers, in direct contrast to the vasoocclusive device of the present invention. No contrary admission should be implied by the arbitrary designation herein of the ends of prior devices of this general type as "proximal" or "distal."

Again, as mentioned above, the vasoocclusive device of the present invention possesses several significant advantages. Most notably, the vasoocclusive device of the present invention enjoys superior and very reliable lodging in the targeted vessel in which it is inserted. The vasoocclusive device of the present invention can be used in vessels of very small diameter, in particular, in cranial vessels having a diameter below about 2.7 mm. Finally, the vasoocclusive device of the present invention can be introduced into a patient by injection with a fluid, rather than by being pushed with a rod or the like.

BRIEF DESCRIPTION OF THE DRAWING

A better understanding of the present invention will now be had upon reference to the following detailed description, when read in conjunction with the accompanying drawing, wherein like reference characters refer to like parts throughout the several views, and in which.

Figure 1:
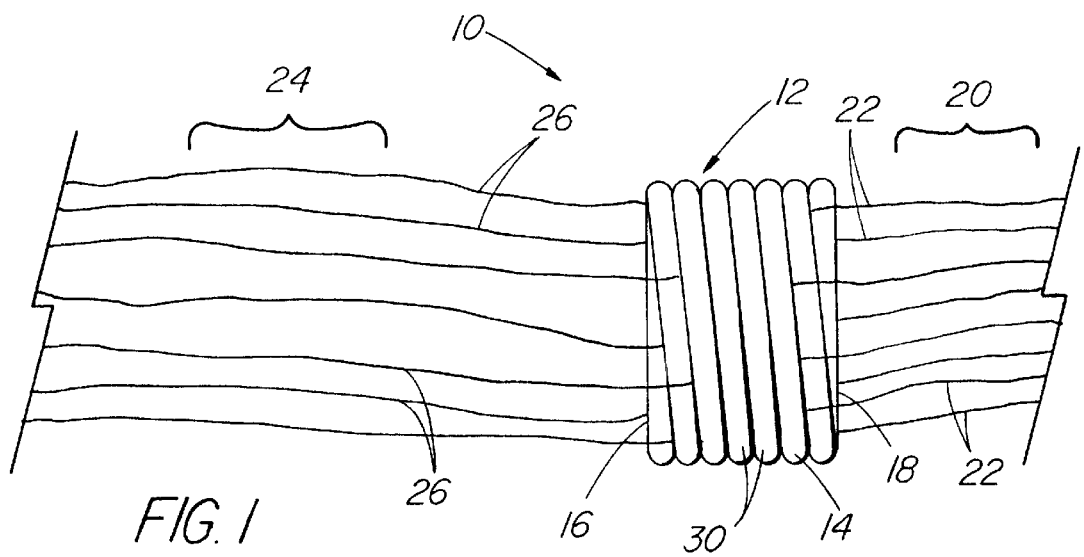
FIG. 1 is a side view of a first preferred embodiment of the vasoocclusive device the present invention.

It will be apparent from the following detailed description that the drawing figures are generally not proportional in their representation of the various elements of the preferred embodiments vasoocclusive device of the present invention.

DETAILED DESCRIPTION

With reference first to FIG. 1, a vasoocclusive device 10 according to the present invention, adapted for introduction into a vessel (not shown) of a human or veterinary patient, is there shown. The vasoocclusive device 10 is capable of occluding a flow in the vessel when introduced into a vessel and first comprises a member 12 having a proximal end 16 and a distal end 18 spaced from the proximal end 16. During use, and in a manner described in more detail below, the distal end 18 of the member 12 is introduced into the vessel before the proximal end 16 of the member 12 is introduced into the vessel.

The vasoocclusive device 10 of the present invention also comprises a distal plurality 20 of fibers associated with an extending away from the distal end 18 of the member 12, as well as a proximal plurality 24 of fibers associated with and extending away from the proximal end 16 of the member 12. The proximal plurality 24 of fibers has an average proximal fiber length which is greater than the average distal fiber length of the distal plurality 20 of fibers. Preferably, the average proximal fiber length is about two to five times the average distal fiber length. However, both the average distal fiber length and the average proximal fiber length preferably are greater than the length of the member 12.

The member 12 can take a variety of shapes and configurations. Preferably, the member 12 is radiopaque and is cylindrical in shape. More preferably, the member 12 comprises a platinum, stainless steel or tungsten coil 14. The coil 14 includes a plurality of windings 30. Although the windings 30 of the coil 14 can be uniformly spaced from one another, the adjacent ones of the windings 30 preferably abut one another.

While the member 12 can be dimensioned to suit any particular vessel of interest, the vasoocclusive device 10 of the present invention finds special utility in the smaller cranial vessels, especially in vessels less than about 2.7 mm in diameter. When intended for use in such vessels, the member 12 of the device 10 is preferably about 1.5 mm to about 3.0 mm long, and more preferably about 2.0 mm long. Conveniently, when configured as the coil 14, the member 12 can be constructed of 0.076 mm (0.003 in.) diameter platinum wire. The wire of the coil 14 can be of circular, rectangular, oval, square, triangular or any other suitable cross-section. Further, again when intended for use in smaller vessels, the member is preferably no more than about 2.7 mm wide, and more preferably about 0.25 mm to about 0.4 mm wide orthogonally with respect to the longitudinal axis.

As mentioned above, however, without regard to the size of the member 12 or the size of the vessel in which it is to be introduced, the characterizing feature of the vasoocclusive device 10 of the present invention is the asymmetrical arrangement of the distal plurality 20 and proximal plurality 24 of fibers on the member 12. The distal and proximal pluralities 20 and 24 of fibers can comprise polyester (for example, DACRON®), nylon, silk or any other medical grade fiber. The proximal plurality 24 of fibers can be formed continuously with the distal plurality 20 of fibers in a manner described in more detail below. Alternatively, the distal plurality 20 of fibers can comprise individual distal fibers 22, and the proximal plurality 24 of fibers can similarly comprise individual proximal fibers 26. Conveniently, 8 to 10 of the individual distal and proximal fibers 22 and 26 can be employed in the device 10, although the exact number can be selected to yield the best lodging of the device 10 in the particular vessel of interest. The individual distal and proximal fibers 22 and 26 are preferably about 40 denier in size. Blood clotting occurs most rapidly, and the best lodging of the device 10 is achieved, when the individual distal and proximal fibers 22 and 26 are small in diameter, and limp enough that the expanded distal and proximal pluralities 20 and 24 of fibers are "fuzzy" when the device 10 is introduced into the vessel.

The average distal fiber length of the distal plurality 20 of fibers, and the average proximal fiber length of the proximal plurality 24 of fibers, are selected to yield good lodging of the device 10 when injected into the vessel. When the member 12 (comprising the coil 14 of 0.076 mm wire) is about 2 mm in length, the average distal fiber length can conveniently be about 6 to 8 mm, and preferably about 7 mm, while the average proximal fiber length can conveniently be about 13 to 15 mm, and preferably about 14 mm. Alternatively, when the coil 14 is made of 0.254 mm (0.010 in.) wire and is about 2 mm long, the average distal fiber length can conveniently be about 4 to 6 mm, and preferably about 5 mm, while the average proximal fiber length can conveniently be about 9 to 11 mm, and preferably about 10 mm. Again, while it appears that an average proximal fiber length that is twice the average distal fiber length may yield the best lodging of the device 10 of the present invention under many circumstances, depending upon the particular vessel targeted for introduction of the device 10 of the present invention, it is expected that the average proximal fiber length can be as high as five times the average distal fiber length.

Figure 2:
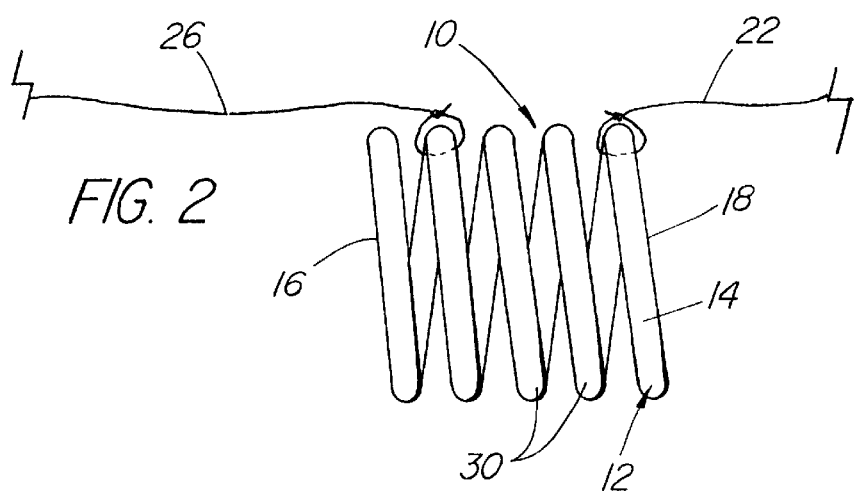
FIGS. 2–5 are side views of other preferred embodiments of the present invention, similar to FIG. 1.

As shown in FIG. 1, the distal and proximal pluralities 20 and 24 of fibers can be attached to the coil 14 by being trapped between adjacent abutting windings 30 of the coil 14. Alternatively, as shown in FIG. 2, when the windings 30 of the coil 14 do not abut one another, the distal and proximal pluralities 20 and 24 of fibers can be looped around or tied to the windings 30 of the coil 14. (For clarity, only single ones of the individual distal and proximal fibers 22 and 26 have been shown in FIG. 2.)

Figure 3:
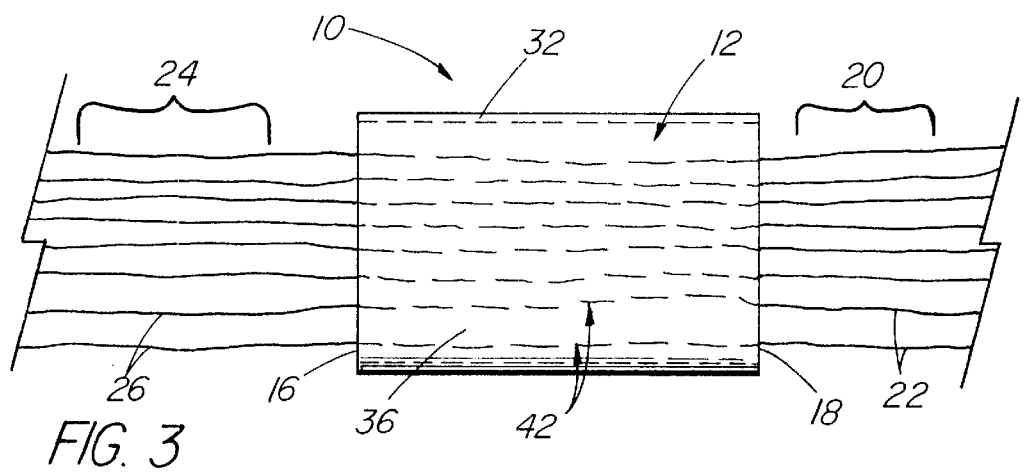
Figure 4:
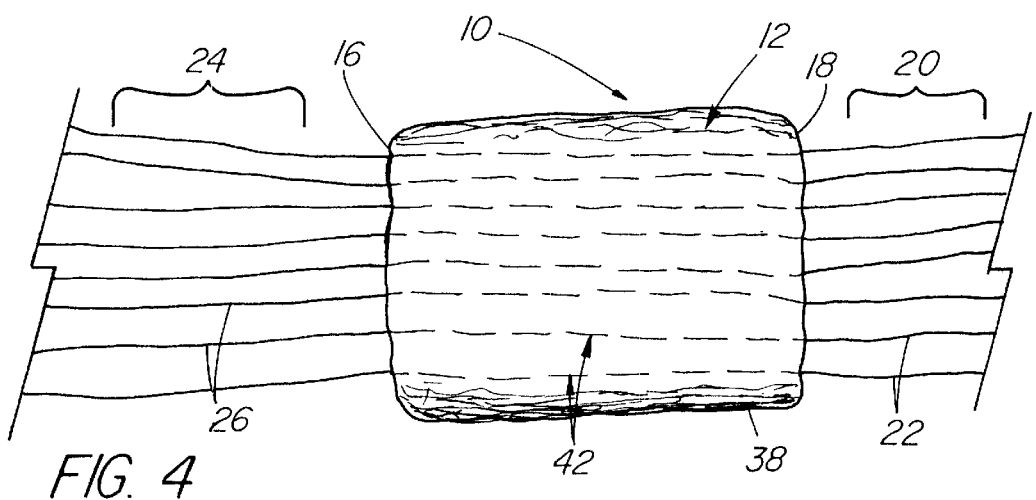
Figure 5:
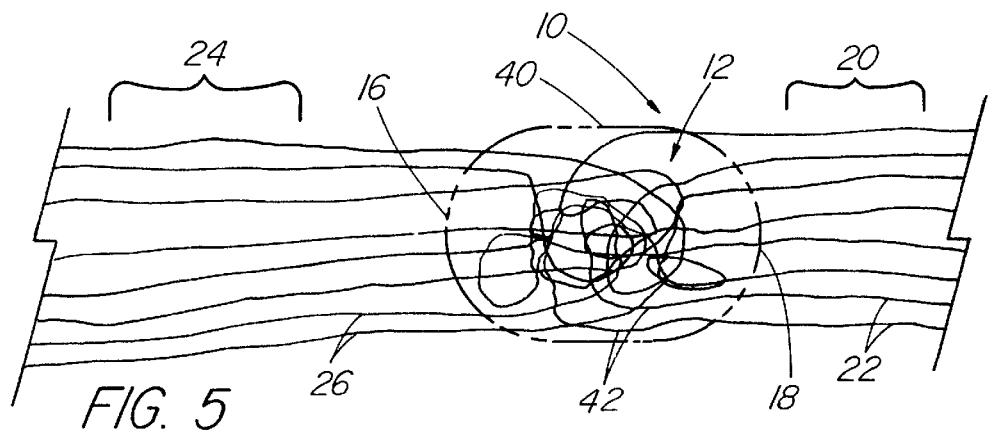

Although the member 12 of the vasoocclusive device 10 of the present invention is preferably the coil 14, the member 12 can be configured in a variety of other ways. For example, as shown in FIG. 3, the member 12 can comprise a segment 32 of cannula, plastic tubing or another generally hollow cylindrical material. Conveniently in such a case, the proximal and distal pluralities 24 and 20 of fibers are formed continuously with one another and comprise a plurality of individual fibers 42. The member 12 then further comprises a means such as glue 36 received in (or, alternatively, applied externally to) the segment 32 for joining the individual fibers 42 to the segment 32. The individual fibers 42 are positioned with respect to the segment 32 so that their unglued portions constitute the proximal and distal pluralities 24 and 20 of fibers. Alternatively, the member 12 can instead comprise a portion of glue 38 (FIG. 4), an enlarged knot 40 (FIG. 5) or the like offset from the centers of the individual fibers 42, joining the individual fibers 42 together. The locus at which the individual fibers 42 are joined will have an appreciable length, at least a few times longer than the diameter of the individual fibers 42, so that the locus of joining constitutes the member 12. Because of this appreciable length, it is sensible to refer to the locus of such joining as having the proximal end 16 and the distal end 18.

Figure 7:
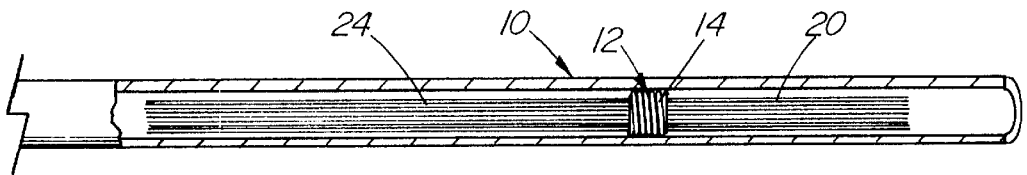
FIG. 7 is a partial cross-sectional view of the distal end of the apparatus of FIG. 6.
Figure 6:
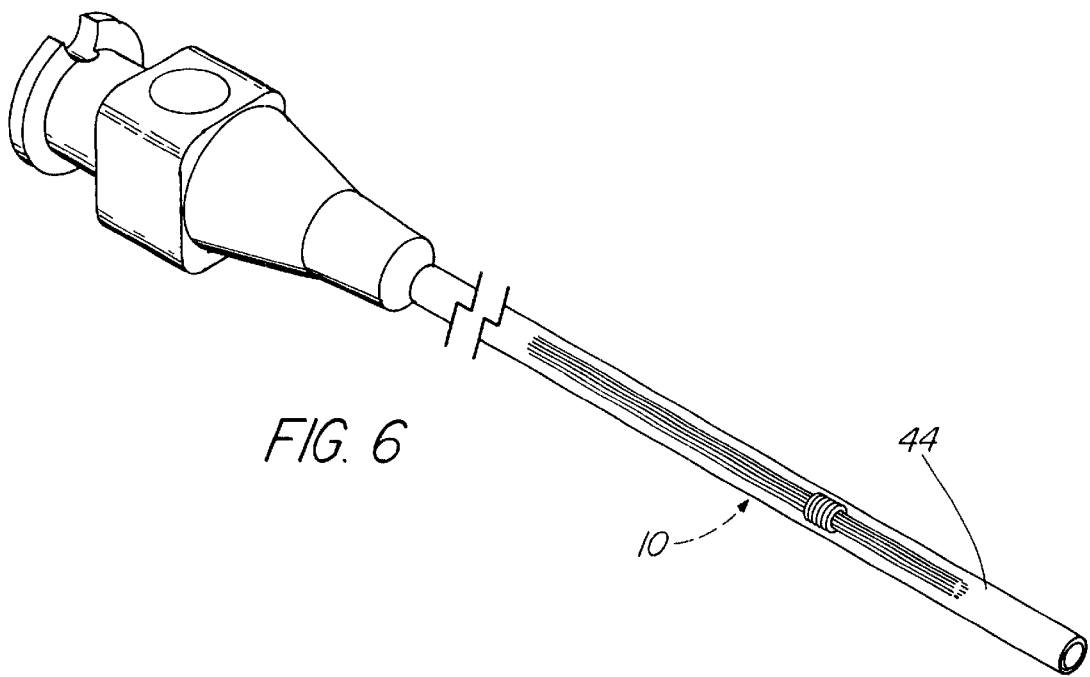
FIG. 6 is a partial cross-sectional view of a portion of an apparatus for injecting any of the preferred embodiments of the vasoocclusive device of the present invention into a human or veterinary patient.

Use of the vasoocclusive device 10 of the present invention can now be readily understood. As shown in the arrangement of FIGS. 6 and 7, the device 10 is disposed in the distal end of a delivery catheter 44, connected to a syringe (not shown) filled with saline, a contrast agent or another appropriate fluid. Access to a target vessel of interest is established by a suitable micro catheter (such as a COOK® MICROFERRET™, not shown). The micro catheter is advanced in the vessel until its distal end is positioned at the site at which it is desired to establish an occlusion. The distal end of the delivery catheter is then connected to the proximal end of the micro catheter, and the syringe actuated to inject the vasoocclusive device 10 out of the catheter 44, through the micro catheter and into the vessel. The drag differential caused by the asymmetric arrangement of the proximal and distal pluralities 24 and 20 of fibers causes the device 10 to reliably lodge in the vessel immediately upon exit from the micro catheter at a location adjacent to the tip of the micro catheter. The micro catheter is then removed from the patient. No pusher rod or wire guide is needed to assist such introduction of the device 10 into the vessel, and the physician is assured that undue downstream migration of the device 10 after injection (but before lodging) will be avoided.

Again, as mentioned above, the vasoocclusive device of the present invention possesses several significant advantages. Most notably, the vasoocclusive device of the present invention enjoys superior and very reliable lodging in the targeted vessel in which it is inserted. The vasoocclusive device of the present invention can be used in vessels of very small diameter, in particular, in cranial vessels having a diameter below about 2.7 mm. Finally, the vasoocclusive device of the present invention can be introduced into a patient by injection with a fluid, rather than by being pushed with a rod or the like.

The details of the construction or composition of the various elements of the vasoocclusive device 10 of the present invention not otherwise disclosed are not believed to be critical to the achievement of the advantages of the present invention, so long as the elements possess the strength or flexibility needed for them to perform as disclosed. The selection of any such details of construction are believed to be well within the ability of one of even rudimentary skills in this area, in view of the present disclosure.

Industrial Applicability

The present invention is useful for forming an occlusion or embolus in a blood vessel or vascular cavity in a human or veterinary patient, and therefore finds applicability in human and veterinary medicine.

It is to be understood, however, that the above-described device is merely an illustrative embodiment of the principles of this invention, and that other devices and methods for using them may be devised by those skilled in the art, without departing from the spirit and scope of the invention. It is also to be understood that the invention is directed to embodiments both comprising and consisting of the disclosed parts.

What is claimed is:

1. A vasoocclusive device (10) adapted for introduction into a vessel of a human or veterinary patient and capable of occluding a flow in the vessel when introduced into the vessel, comprising:

a member (12) having a proximal end (16) and a distal end (18) spaced from the proximal end (16), the distal end (18) of the member (12) being introduced into the vessel before the proximal end (16) of the member (12) is introduced into the vessel;

a distal plurality (20) of fibers having an average distal fiber length, the distal plurality (20) of fibers being associated with and extending away from the distal end (18) of the member (12); and a proximal plurality (24) of fibers having an average proximal fiber length, the proximal plurality (24) of fibers being associated with and extending away from the proximal end (16) of the member (12);

wherein the average distal fiber length is greater than the length of the member, and the average proximal fiber length is at least twice the average distal fiber length.

2. The device (10) according to claim 1, wherein the average proximal fiber length is up to about five times the average distal fiber length.

3. The device (10) according to claim 1, wherein the member (12) is cylindrical in shape.

4. The device (10) according to claim 1, wherein the member (12) is radiopaque.

5. The device (10) according to claim 1, wherein the member (12) comprises platinum, stainless steel or tungsten.

6. The device (10) according to claim 1, wherein the member (12) is about 1.5 mm to about 3.0 mm long between the proximal end and the distal end thereof.

7. The device (10) according to claim 1, wherein the average distal fiber length is about 4 mm to about 8 mm, and the average proximal fiber length is about 9 mm to about 15 mm.

8. The device (10) according to claim 1, wherein the distal plurality (20) of an fibers and the proximal plurality (24) of fibers comprise polyester, nylon or silk.

9. The device (10) according to claim 1, wherein the distal plurality (20) of fibers comprises 8 to 10 individual distal fibers (22), and the proximal plurality (24) of fibers comprises 8 to 10 individual proximal fibers (26).

10. The device (10) according to claim 1, wherein the distal plurality (20) of fibers comprises individual distal fibers (22) of about 40 denier, and the proximal plurality (24) of fibers comprises individual proximal fibers (26) of about 40 denier.

11. The device (10) according to claim 1, wherein the proximal plurality (24) of fibers is formed continuously with the distal plurality (20) of fibers.

12. The device (10) according to claim 1, wherein the distal plurality (20) and proximal plurality (24) of fibers comprise a plurality of individual fibers (42), and wherein the member (12) comprises glue (36, 38) or a knot (40) joining the individual fibers (42) in an offset manner.

13. The device (10) according to claim 1, wherein the member (12) is a coil (14).

14. The device (10) according to claim 1, wherein the coil (14) includes a plurality of abutting windings (30).

15. The device (10) according to claim 14, wherein the distal plurality (20) of fibers and the proximal plurality (24) of fibers are trapped between abutting windings (30) of the coil (14).

16. The device (10) according to claim 1, wherein the member (12) is no more than about 2.7 mm wide orthogonally with respect to the longitudinal axis.

17. The device (10) according to claim 1, wherein the member (12) is about 0.25 mm to about 0.4 mm wide orthogonally with respect to the longitudinal axis.

18. The device of claim 1 wherein both the average distal fiber length and the average proximal fiber length are greater than twice the length of the member.

19. A vasoocclusive device (10) adapted for introduction into a vessel of a human or veterinary patient and capable of occluding a flow in the vessel when introduced into the vessel, comprising:
 a radiopaque member (12) having a proximal end (16) and a distal end (18) spaced from the proximal end (16), the distal end (18) of the member (12) being introduced into the vessel before the proximal end (16) of the member (12) is introduced into the vessel, and the member (12) being about 1.5 mm to about 3.0 mm in length between the distal end and the proximal end thereof;
 a distal plurality (20) of fibers having an average distal fiber length, the distal plurality (20) of fibers being associated with and extending away from the distal end (18) of the member (12); and
 a proximal plurality (24) of fibers having an average proximal fiber length, the proximal plurality (24) of fibers being associated with and extending away from the proximal end (16) of the member (12);
  wherein the average proximal fiber length is about two to about five times the average distal fiber length, the average distal fiber length is about 4 mm to about 8 mm and the average proximal fiber length is about 9 mm to about 15 mm;
  wherein the average distal fiber length and the average proximal fiber length are both greater than the length of the member (12);
  wherein the member (12) comprises a cylindrical coil of platinum, stainless steel or tungsten including a plurality of abutting windings (30);
  wherein the distal plurality (20) of fibers comprises 8 to 10 individual distal fibers (22) comprising polyester, nylon or silk of about 40 denier, and the proximal plurality (24) of fibers comprises 8 to 10 individual proximal fibers (26) comprising polyester, nylon or silk of about 40 denier; and
  wherein the member (12) is about 0.25 mm to about 0.4 mm wide orthogonally with respect to the longitudinal axis.

20. In a vasoocclusive device (10) adapted for introduction into a vessel of a human or veterinary patient and capable of occluding a flow in the vessel when introduced into the vessel, the device (10) comprising: a member (12) having a proximal end (16) and a distal end (18) spaced from the proximal end (16), the distal end (18) of the member (12) being introduced into the vessel before the proximal end (16) of the member is introduced into the vessel; a distal plurality (20) of fibers having an average distal fiber length, the distal plurality (20) of fibers being associated with and extending away from the distal end (18) of the member (12); and a proximal plurality (24) of fibers having an average proximal fiber length, the proximal plurality (24) of fibers being associated with and extending away from the proximal end (16) of the member (12); the improvement wherein the average distal fiber length is greater than the length of the member, and the average proximal fiber length is at least two times the average distal fiber length.

21. The device of claim 20 wherein the average proximal fiber length is between two times and five times the average distal fiber length.

22. The device of claim 20 wherein both the average distal fiber length and the average proximal fiber length are greater than twice the length of the member.

23. In a vasoocclusive device adapted for introduction into a vessel of a human or veterinary patient by a delivery catheter and capable of occluding a flow in the vessel when introduced into the vessel at a treatment site by use of fluid injected into the delivery catheter, the device comprising a member having a proximal end and a distal end spaced from the proximal end, the distal end of the member being introduced into the vessel before the proximal end of the member is introduced into the vessel; a distal plurality of fibers having an average distal fiber length, the distal plurality of fibers being associated with and extending away from the distal end of the member; and a proximal plurality of fibers having an average proximal fiber length, the proximal plurality of fibers being associated with and extending away from the proximal end of the member; the improvement wherein both the average proximal fiber length and the average distal fiber length are at least two times the length of the member, and the fiber lengths are sufficiently long to interact with blood flowing through the vessel to immediately and reliably lodge the device at the treatment site in the vessel and block the flow of blood.

24. An arrangement of a delivery catheter and a vasoocclusive device adapted for introduction into a vessel of a human or veterinary patient by fluid injected into the catheter, and capable of occluding a flow in the vessel when introduced into the vessel, comprising:

a delivery catheter having a distal end for insertion into vasculature of a patient, and a vasoocclusive device disposed within said delivery catheter and urgeable from said distal end during placement of the device at a treatment site by injection fluid injected into the catheter proximally of the device, the vasoocclusive device comprising a member having a proximal end and a distal end spaced from the proximal end, the distal end of the member being proximate the distal end of the catheter to be introduced during placement into the vessel before the proximal end, a distal plurality of fibers having an average distal fiber length, the distal plurality of fibers extending away from the distal end of the member, and a proximal plurality of fibers having an average proximal fiber length, the proximal plurality of fibers extending away from the proximal end of the member, wherein the average proximal fiber length is greater than the average distal fiber length, such that during release of the device into the vessel by hydraulic urging, the lesser length distal fibers tend to increase drag in the blood flowing in the vessel and slow the device, and the greater length proximal fibers then cause blood flow in the vessel to increase pressure on the device resulting in the device lodging immediately and reliably to block blood flow through the vessel.

25. The arrangement of claim 24 wherein the average proximal fiber length is about two to about five times the average distal fiber length.

26. The arrangement of claim 24 wherein both the average distal fiber length and the average proximal fiber length are greater than the length of the member.

27. The arrangement of claim 24 wherein the member is about 1.5 mm to about 3.0 mm long between the proximal end and the distal end thereof.

28. The arrangement of claim 24 wherein the average distal fiber length is about 4 mm to about 8 mm, and the average proximal fiber length is about 9 mm to about 15 mm.

29. The arrangement of claim 24 wherein the distal plurality of fibers and the proximal plurality of fibers comprise polyester, nylon or silk.

30. The arrangement of claim 24 wherein the distal plurality of fibers comprises eight to ten individual distal fibers, and the proximal plurality of fibers comprises eight to ten individual proximal fibers.

31. The arrangement of claim 24 wherein the distal plurality of fibers comprises individual distal fibers of about 40 denier, and the proximal plurality of fibers comprises individual proximal fibers of about 40 denier.

32. The arrangement of claim 24 wherein the proximal plurality of fibers is formed continuously with the distal plurality of fibers.

33. The arrangement of claim 24 wherein the distal plurality of fibers and proximal plurality of fibers comprise a plurality of individual fibers, and wherein the member comprises glue or a knot joining the individual fibers in an offset manner.

34. The arrangement of claim 24 wherein the member is a coil.

35. The arrangement of claim 24 wherein the member is no more than about 2.7 mm orthogonally to the longitudinal axis.

36. The arrangement of claim 24 wherein the member is about 0.25 mm to about 0.4 mm wide orthogonally to the longitudinal axis.

* * * * *